United States Patent [19]

Röchling et al.

[11] 3,997,534
[45] Dec. 14, 1976

[54] SUBSTITUTED TRIAZINO-BENZIMIDAZOLES

[75] Inventors: Hans Röchling, Altenhain, Taunus; Kurt Härtel, Hofheim, Taunus; Reinhard Kirsch, Niederjosbach, Taunus; Dieter Düwel, Hofheim, Taunus, all of Germany

[73] Assignee: Hoechst Aktiengesellschaft, Frankfurt am Main, Germany

[22] Filed: Nov. 7, 1974

[21] Appl. No.: 521,899

[30] Foreign Application Priority Data

Nov. 10, 1973 Germany .......................... 2356258

[52] U.S. Cl. ...................... 260/249.5; 260/247.5 C
[51] Int. Cl.² ........................................ C07D 251/72
[58] Field of Search ................. 260/249.5, 247.5 C

[56] References Cited

UNITED STATES PATENTS

| 2,016,521 | 10/1935 | Steindorff et al. | 260/248 X |
| 3,896,120 | 7/1975 | Rochling et al. | 260/249.5 |

*Primary Examiner*—John M. Ford
*Attorney, Agent, or Firm*—Curtis, Morris & Safford

[57] ABSTRACT

The present invention relates to triazinobenzimidazoles and to a process for their preparation.

The compounds are chemotherapeutics and are suitable for combating parasitary diseases in humans and animals; they are especially active against nematodes.

17 Claims, No Drawings

SUBSTITUTED TRIAZINO-BENZIMIDAZOLES

The invention relates to triazino-benzimidazoles of the formula

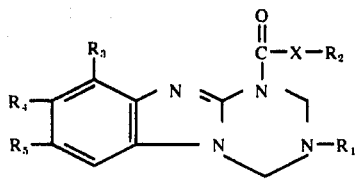

in which $R_1$ can denote an optionally branched alkyl group with 1 to 18 C atoms, an optionally branched alkenyl group with 3 to 18 C atoms, a cycloalkyl group with 3 to 12 C atoms, which can also be substituted by one or more alkyl groups with 1 to 4 C atoms or by the hydroxyl group, a radical of the formula

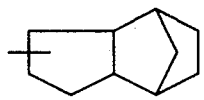

(tricyclo-$[5,2,1,0^{2,6}]$-decyl), a phenalkyl or diphenylalkyl group which in each case has 1 to 6 C atoms in the alkylene radical and in which the phenyl nuclei can be substituted by halogen, $(C_1-C_4)$-alkyl, $(C_1-C_4)$-alkoxy or $(C_1-C_4)$-alkylthio, a phenyl or naphthyl group which can be substituted by $(C_1-C_4)$-alkyl, halogen, $(C_1-C_4)$-halogenoalkyl, hydroxyl, $(C_1-C_4)$-alkoxy, phenoxy or $(C_1-C_4)$-alkylthio, or a hydroxyalkyl, alkoxyalkyl, polyalkoxyalkyl, alkylmercaptoalkyl, dialkylphosphinylalkyl, furfuryl, morpholinoalkyl, pyrrolidinoalkyl, piperidinoalkyl or carbalkoxyalkyl group with 2 to 12 C atoms, or $R_1$ denotes a dialkylaminoalkyl group of the formula

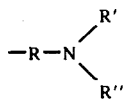

in which R denotes a straight-chain or branched $(C_2-C_6)$-alkylone group and R' and R'' denote identical or different $(C_1-C_4)$-alkyl radicals, or $R_1$ denotes a 1',1'-dialkyl-substituted propin-2'-yl radical of the general formula

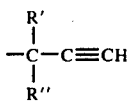

with R' and R'' = $(C_1-C_4)$-alkyl or optionally substituted phenyl, but preferably $(C_1-C_4)$-alkyl and especially $(C_1-C_2)$-alkyl, or can be a $(C_2-C_3)$-alkinyl-substituted $(C_5-C_8)$-cycloalkyl radical, or denotes a bicycloheptenylmethyl, an exo- or endo-bicycloheptylmethyl, a bicycloheptyl or tricyclo-decenyl radical, $R_2$ can be a straight-chain or branched $(C_1-C_6)$-alkyl group, $R_3$ denotes hydrogen or halogen, preferably chlorine or bromine, $R_4$ denotes hydrogen or halogen, preferably fluorine, chlorine or bromine, or the phenylthio, phenylsulfinyl, phenoxy ethoxy, methyl, nitrile, nitro, quinolinoxy, N'-methylpiperazine or benzoyl group, $R_5$ denotes hydrogen or halogen, preferably chlorine or bromine, and X denotes oxygen or sulphur; compounds excepted are those of the general formula I, wherein $R_3$, $R_4$ and $R_5$ all denote hydrogen, X denotes oxygen and $R_2$ denotes methyl.

Preferred combinations of $R_3$, $R_4$ and $R_5$ are those in which at least one of the radicals $R_3$, $R_4$ and $R_5$ is hydrogen, and if $R_4$ is —SR or —OR, $R_3$ and $R_5$ are preferably hydrogen. Hence, preferred combinations are those in which $R_3$, $R_4$ and $R_5$ denote hydrogen or in which $R_3$ and $R_5$ denote hydrogen and $R_4$ denotes phenylthio, phenylsulfinyl, phenoxy, ethoxy, chlorine, fluorine, bromine, nitrile or methyl, or in which $R_4$ and $R_5$ are hydrogen and $R_3$ is halogen, preferably chlorine, or $R_4$ is hydrogen and $R_3$ and $R_5$ are halogen, preferably bromine, or $R_3$ is hydrogen and $R_4$ and $R_5$ are halogen, preferably chlorine. If X denotes sulphur, $R_3$, $R_4$ and $R_5$ are preferably hydrogen.

A further subject of the invention is a process for the manufacture of compounds of the formula I, wherein the substituents have the abovementioned meanings, which is characterised in that a benzimidazole of the formula

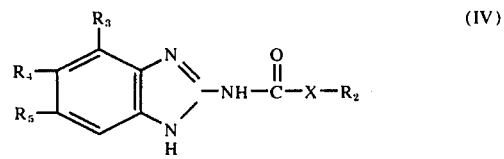

is reacted with an amine of the formula $H_2N—R_1$, wherein $R_1$ has the abovementioned meaning, and with formaldehyde.

A suitable embodiment of the process is to suspend or to dissolve the benzimidazole IV in a solvent, add one mol of the amine and then add 2 to 4 mols of aqueous formaldehyde solution while stirring. The reaction is carried out at a temperature of between 0° and 80° C, preferably between 20° and 40° C, but the temperature range is not critical. In general, the reaction product dissolves and can, in this solution, be separated from any undissolved benzimidazole of the formula IV which may still be present, for example by filtration. The triazinobenzimidazole (I) can be isolated in a pure form by concentrating the solution and treating the residue with an inert solvent such as benzene, or by reprecipitation, for example from methylene chloride/benzene.

Even if a less than equivalent amount of formaldehyde is used, the reaction results in the formation of the end product I.

Solvents which can be used for the reaction are in particular moderately polar or weakly polar solvents, preferably with low boiling points, such as methylene chloride, chloroform, carbon tetrachloride, benzene, ethers such as diethyl ether, diisopropyl ether and tetrahydrofurane, esters such as methyl acetate and ethyl acetate or ketones such as acetone or methyl ethyl ketone. Chloroform or methylene chloride is employed preferentially.

The benzimidazoles IV used as starting materials can be manufactured, for example, according to the method described in J. Am. Chem. Soc. 56, 144 (1934) for 2-methoxycarbonylamino-benzimidazole, by reaction of appropriately substituted o-phenylenediamines with S-methyl-isothioureadicarboxylic acid dialkyl esters or with S-methyl-isothioureadicarboxylic acid dithioalkyl esters. The amines required for the reaction are manufactured according to processes which are known from, for example, Houben-Weyl "Methoden der organischen Chemie" ("Methods of Organic Chemistry"), volume 11/1, Stuttgart 1957, and from Weygand-Hilgetag "Organisch chemische Experimentierkunst" ("Experimental Technique in Organic Chemistry"), Leipzig 1964, pages 490–729.

The new triazino-benzimidazoles of the formula I are valuable chemotherapeutic agents and can be used for combating parasitary diseases in humans and animals, for example in test animals. These new compounds are active against nematodes, such as, for example, against various species of Trichostrongylidae and Strongylidae of the digestive tract of farm animals. In addition to being active against nematodes of the intestine, they also process a good activity against nematodes of which the development stages reside transiently or permanently in other body tissues or body organs (such as, for example, lungs and muscle). In addition, the new compounds are also active against cestodes.

The compounds have a particularly pronounced activity against strongylides of the stomach and intestine, which attack, above all, ruminants. They are also active against hookworms which are parasitic principally in humans and carnivores. Both types of parasites cause considerable damage to health and considerable economic losses. The new compounds can be used as anthelmintics in human medicine and veterinary medicine.

The invention therefore also relates to pharmaceutical agents, especially anthelmintic agents which contain the triazinobenzimidazoles (I) as active compounds, generally in concentrations of 2 to 96 per cent by weight, in the customary mixtures with solid or liquid inert, or physiologically tolerated, auxiliaries such as, for example, Tylose (sodium carboxymethyl cellulose). 2–30 % by weight of a triazinobenzimidazole (I) are preferred for oral administration and 50–70% by weight for parenteral administration.

The active compounds are administered orally or subcutaneously, together with suitable pharmaceutical solvents or excipients. For oral administration, suspensions with 1–50% by weight of active compound, preferably 5–20% by weight of active compound, or powders, suspened in water, with 1–80, preferably 40–70, % by weight of active compound, and also pastes or granules, can be ued. Sterile solutions are used for parenteral treatment.

The compounds claimed are furthermore distinguished by a fungicidal, especially plant-systemic, action, so that they can also be used to combat fungal pathogens which have already penetrated into the plant tissue. This is particularly important in the case of those fungal diseases which have a long incubation time and which can no longer be combatted with customary fungicides after the infection has taken place. These compounds have a very broad spectrum of action which covers a whole series of important fungal pathogens which are important in agriculture, fructiculture, viniculture, hop culture, gardening and garden nurseries, and of which Fusicladium, Gloeosporium, Cylindrosporium, Botrytis, Cercospora, Septoria, Mycosphaerella, Gladosporium, Colletotrichum, Rhizoctonia, Fusarium, Cercosporella, Ustilagineae, Erysiphaceae, Aspergillaceae, Sclerotinaceae and Verticillium may be mentioned as just a few examples.

In addition, a number of the new compounds of the formula I, especially those with long-chain radicals $R_1$, have a good action against Phycomycetes, such as species of Peronospora and species of Phytophtora.

The new compounds of the formula I can also be used to protect stored fruit and vegetables against fungal attack, for example against species of Fusarium and species of Penicillium. They are also suitable for the protection of textiles, timber, dyestuffs and paint films against attack by rotting organisms and other fungal organisms.

A further subject of the invention are therefore pesticides, especially fungicidal agents, which contain the triazinobenzimidazoles of the general formula I as active compounds, in general in concentrations of 2 to 90% by weight, preferably 10 to 80% by weight, mixed with customary solid or liquid inert carriers, adhesives, wetting agents, dispersing agents and/or grinding auxiliaries.

They can be used as spraying powders, emulsions, suspensions, dusts or granules. They can also be mixed with other fungicides with which they form compatible mixtures.

Carriers which can be used are mineral substances such as aluminum silicates, aluminas, kaolin, chalks, siliceous chalks, talc, kieselguhr or hydrated silica, or preparations of these mineral substances which contain special additives, for example chalk lubricated with sodium stearate.

Vehicles which can be used for liquid preparations are all customary and suitable solvents, for example toluene, xylene, diacetone-alcohol, cyclohexanone, isophorone, benzines, paraffin oils, dioxane, dimethylformamide, dimethylsulphoxide, ethyl acetate, tetrahydrofurane, chlorobenzene and others.

Adhesives which can be used are glutinous cellulose products or polyvinyl alcohols.

Wetting agents which can be used are all suitable emulsifiers, such as oxethylated alkylphenols, salts of arylsulphonic acids or alkylarylsulphonic acids, salts of oleylmethyl-taurine, salts of oxethylated phenylsulphonic acids or soaps.

Suitable dispersing agents are cell pitch (salts of ligninsulphonic acid), salts of naphthalenesulphonic acid or salts of oleyl-methyl-taurine.

Grinding auxiliaries which can be used are suitable inorganic or organic salts such as sodium sulfate, ammonium sulfate, sodium carbonate, sodium bicarbonate, sodium thiosulfate, sodium stearate or sodium acetate.

Amongst the compounds of the formula I, those particularly preferred as chemotherapeutics and plant protection agents are those in which X denotes oxygen and $R_2$ denotes methyl, and either $R_3$ denotes chlorine and $R_4$ and $R_5$ denote hydrogen, or $R_3$ and $R_5$ represent hydrogen and $R_4$ represents phenylthio, ethoxy, phenoxy, benzoyl or N-methyl-piperazinyl

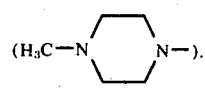

The preparation examples and use examples which follow illustrate the invention:

A. PREPARATION EXAMPLES

Example 1

25.0 g (0.084 mol) of 2-methoxycarbonylamino-5-phenylthio-benzimidazole are suspended in 300 ml of methylene chloride and 8.28 g (0.084 mol) of cyclohexylamine are added.

The mixture is warmed to 35° C and 16.7 ml of 35% strength formaldehyde solution are slowly added dropwise at this temperature. Thereafter the mixture is stirred for 2 hours at 38° C and then allowed to cool while stirring. The unconverted benzimidazole is filtered off (0.5 g after drying), the aqueous layer is separated off and the methylene chloride solution is dried over magnesium sulfate. After concentration, an oil is obtained, which becomes crystalline on dissolving in methylene chloride and precipitating with petroleum ether at 80°–110° C.

Yield: 21 g (59.4% of theory). Melting point: 118°–120° C.

1-Methoxycarbonyl-3-cyclohexyl-7-phenylthio-S-hexahydro-triazino-benzimidazole

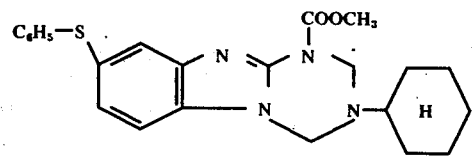

$C_{23}H_{26}N_4O_2S$: molecular weight 422.

Calculated: C, 65.42%; H, 6.6%; N, 13.25%. Found: C, 65.6%; H, 6.6%; N, 13.2%.

Example 2

22.5 g (0.1 mol) of 2-methoxycarbonylamino-4-chlorobenzimidazole are suspended in 300 ml of methylene chloride and 7.3 g (0.1 mol) of tert.-butylamine are added. The mixture is warmed to 30° C, 20 ml of 35% strength formaldehyde solution are added dropwise at this temperature and the mixture is then warmed to 38° C for 2 hours.

After cooling, the aqueous layer is separated off and the methylene chloride phase is dried over magnesium sulfate.

After concentrating, an oil is obtained, which solidifies on stirring with benzine.

Yield: 26 g (80.7% of theory). Melting point: 114°–115° C. 1-Methoxycarbonyl-3-tert.-butyl-8-chloro-S-hexahydrotriazino-benzimidazole

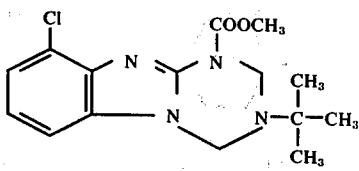

$C_{15}H_{19}ClN_4O_2$: molecular weight 322.5.
Calculated: C, 55.35%; H, 5.8%; N, 17.11%.
Found: C, 55.5%; H, 5.9%; N, 17.1%.

The compounds listed in the table which follows were prepared analogously to examples (1) and (2):

Table

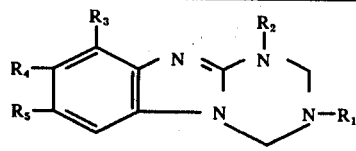

| Example | $R_1$ | $R_2$ | $R_3$ | $R_4$ | $R_5$ | Melting point (° C) |
|---|---|---|---|---|---|---|
| 3 | $C_4H_9n$ | $COOCH_3$ | H | $C_6H_5O-$ | H | non-distillable oil |
| 4 | $-(CH_2)_{11}-CH_3$ | $COOCH_3$ | H | CN | H | 89–91 |
| 5 | $-(CH_2)_{11}-CH_3$ | $COOCH(CH_3)_2$ | H | H | H | 72–73 |
| 6 | $-(CH_2)_{11}-CH_3$ | $COOC_3H_7$ | H | H | H | 47–48 |
| 7 | cyclohexyl | $COOCH_3$ | H | CN | H | 163–165 |
| 8 | $-(CH_2)_{11}-CH_3$ | $COOC_2H_5$ | H | H | H | non-distillable oil |
| 9 | cyclohexyl | $COOC_4H_9$ | H | H | H | 130–132 |
| 10 | cyclohexyl | $CO-S-C_2H_5$ | H | H | H | 117–119 |
| 11 | $-(CH_2)_{11}-CH_3$ | $CO-S-C_2H_5$ | H | H | H | 40–43 |
| 12 | $-(CH_2)_{11}-CH_3$ | $COOC_4H_9n$ | H | H | H | 106 |
| 13 | $-(CH_2)_{11}-CH_3$ | $COO(CH_2)_2-CH(CH_3)_2$ | H | H | H | non-distillable oil |

Table-continued

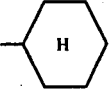

| Example | $R_1$ | $R_2$ | $R_3$ | $R_4$ | $R_5$ | Melting point (° C) |
|---|---|---|---|---|---|---|
| 14 | cyclohexyl | $COOCH_3$ | Cl | H | H | 133–134 |
| 15 | cyclohexyl | $CO-S-CH_3$ | H | H | H | 76 (decomposition) |
| 16 | cyclohexyl | $COOC_2H_5$ | H | H | H | 104 |
| 17 | $-C_4H_9 n$ | $COOC_2H_5$ | H | H | H | 84 |
| 18 | $-(CH_2)_{11}-CH_3$ | $COOCH_3$ | Cl | H | H | 127–128 |
| 19 | $-C_4H_9 n$ | $COOCH_3$ | H | $NO_2$ | H | 125–130 |
| 20 | cyclohexyl | $COOCH_3$ | Cl | H | Cl | 160–163 |
| 21 | $-(CH_2)_{11}-CH_3$ | $COOCH_3$ | Cl | H | Cl | 101–102 |
| 22 | $-C_4H_9 n$ | $COOC_4H_9 n$ | H | H | H | 106–108 |
| 23 | $-(CH_2)_{11}-CH_3$ | $CO-S-CH_3$ | H | H | H | 39–41 |
| 24 | $-C_4H_9 iso$ | $COOC_4H_9 n$ | H | H | H | 118–120 |
| 25 | cyclohexyl | $COOCH_3$ | Br | H | Br | 148–151 |
| 26 | $-(CH_2)_{11}-CH_3$ | $COOCH_3$ | Br | H | Br | 97–98 |
| 27 | $-(CH_2)_{11}-CH_3$ | $COOCH_3$ | H | F | H | 80–82 |
| 28 | $-CH_2-CH(CH_3)_2$ | $CO-S-CH_3$ | H | H | H | 120–124 |
| 29 | cyclohexyl | $COOCH_3$ | H | F | H | 145–146 |
| 30 | $-C_4H_9 n$ | $CO-S-CH_3$ | H | H | H | non-distillable oil |
| 31 | $-CH_2-CH(CH_3)_2$ | $COOCH_3$ | H | $-S-C_6H_5$ | H | 106–107 |
| 32 | $-C_4H_9 iso$ | $COOC_2H_5$ | H | H | H | 115 |
| 33 | cyclohexyl | $COOCH_3$ | H | Cl | Cl | 197–200 |
| 34 | $-CH_2-CH(CH_3)_2$ | $COOCH_3$ | H | Cl | H | 138–139 |
| 35 | $-(CH_2)_{11}-CH_3$ | $COOCH_3$ | H | $CH_3$ | H | 74–76 |
| 36 | $-CH_2-CH(CH_3)_2$ | $COOCH_3$ | H | $CH_3$ | H | 118–121 |
| 37 | cyclohexyl | $COOCH_3$ | H | $CH_3$ | H | 146–148 |
| 38 | $-(CH_2)_{11}-CH_3$ | $COOCH_3$ | H | Cl | H | 82–83 |

Table-continued

[Structure: benzene ring with R3, R4, R5 substituents, connected via N=C(R2)-N to a piperazine ring with N-R1]

| Example | R₁ | R₂ | R₃ | R₄ | R₅ | Melting point (° C) |
|---|---|---|---|---|---|---|
| 39 | cyclohexyl-H | COOCH₃ | H | Cl | H | 178–179 |
| 40 | —C₄H₉n | COOCH₃ | H | CH₃ | H | 105–106 |
| 41 | —C₄H₉n | COOCH₃ | H | Cl | Cl | 142–144 |
| 42 | —(CH₂)₁₁—CH₃ | COOCH₃ | H | Cl | Cl | 98 |
| 43 | cyclohexyl-H | COOCH₃ | H | Cl | Cl | 219–220 |
| 44 | —CH₂—CH(CH₃)₂ | COOCH₃ | H | OC₂H₅ | H | 86–90 |
| 45 | —(CH₂)₁₁—CH₃ | COOCH₃ | H | OC₂H₅ | H | 97–98 |
| 46 | cyclohexyl-H | COOCH₃ | H | OC₂H₅ | H | 105–106 |
| 47 | —CH₂—CH(CH₃)₂ | COOCH₃ | Cl | H | H | 154–155 |
| 48 | —C(CH₃)₃ | COOCH₃ | Cl | H | H | 114–115 |
| 49 | —(CH₂)₇—CH₃ | COOCH₃ | Cl | H | H | 124–125 |
| 50 | —C₄H₉iso | COOCH₃ | Cl | H | H | 138–139 |
| 51 | —CH₃ | COOCH₃ | Cl | H | H | 161–162 |
| 52 | —(CH₂)₂—CH₃ | COOCH₃ | Cl | H | H | 140–141 |
| 53 | —C(CH₃)₃ | COOCH₃ | H | —S—C₆H₅ | H | 158–159 |
| 54 | —CH₂—C₆H₅ (benzyl) | COOCH₃ | H | —S—C₆H₅ | H | 145–150 |
| 55 | —(CH₂)₁₁—CH₃ | COOCH₃ | H | —S—C₆H₅ | H | 76–78 |
| 56 | phenyl | COOCH₃ | Cl | H | H | 154–156 |
| 57 | —C₁₈H₃₇ | COOCH₃ | Cl | H | H | 105–106 |
| 58 | —C₉H₁₉iso | COOCH₃ | H | —S—C₆H₅ | H | non-distillable oil |
| 59 | —CH(C₆H₅)—CH₂—C₆H₅ | COOCH₃ | H | —S—C₆H₅ | H | 86–90 |
| 60 | tricyclic (norbornyl-fused) | COOCH₃ | H | —S—C₆H₅ | H | 73–76 |
| 61 | —(CH₂)₃—S—CH₃ | COOCH₃ | H | —S—C₆H₅ | H | non-88–91 |
| 62 | —C₁₈H₃₇ | COOCH₃ | H | —S—C₆H₅ | H | non-distillable oil |
| 63 | —(CH₂)₇—CH₃ | COOCH₃ | H | —S—C₆H₅ | H | non-distillable oil |
| 64 | cyclohexyl-H | COOCH₃ | H | —O—(decahydroquinolinyl) | H | 150–160 (decomposition) |

Table-continued

[Structure: substituted benzene ring with R₃, R₄, R₅ substituents, attached to N=C(NR₂-CH₂-CH₂-NR₁) cyclic amidine group]

| Example | R₁ | R₂ | R₃ | R₄ | R₅ | Melting point (° C) |
|---|---|---|---|---|---|---|
| 65 | cyclohexyl (H) | COOCH₃ | H | —CO—C₆H₅ | H | 195–197 (decomposition) |
| 66 | cyclohexyl (H) | COOCH₃ | H | —N(CH₂CH₂)₂N—CH₃ (N-methylpiperazinyl) | H | 137–140 (decomposition) |
| 67 | —CH₃ | COOCH₃ | H | —S—C₆H₅ | H | 115–117 |
| 68 | phenyl | COOCH₃ | H | —S—C₆H₅ | H | 56–62 |
| 69 | cyclohexyl (H) | COOCH₃ | H | —SO—C₆H₅ | H | 168–172 |

Example 68

12 g of active compound according to Preparation Example (1) are pre-ground with 3 g of highly disperse silica and then mixed uniformly with 45 g of a preground mixture of 10 g of cell pitch, 49 g of magnesium aluminum silicate, 8 g of highly disperse silica, 7 g of polypropylene glycol P 750 + highly disperse silica (1 : 1) and 1 g of oleic acid methyl-tauride. 60 g of a 20% strength spraying powder are thus obtained.

B. USE EXAMPLES

1. Fungicidal action

Example I

Wheat plants in the 3-leaf stage were heavily infected with conidia of wheat mildew and then brought into a greenhouse which was at a relative atmospheric humidity of 70 –80% and a temperature of 21° C. 3 days after the infection, the plants were treated with the compounds claimed, according to Preparation Example (14), (18) and (46), using amounts of 250, 125, 60 and 30 mg of active compound/liter of spray liquor, until dripping wet. The comparison agent used was a commercially available product based on Benomyl, (1-N-butylcarbamoyl-2-methoxycarbonylamino-benzimidazole), containing the same amounts of active compound.

After an incubation time of 7 days, the plants were examined for attack by mildew. The results in Table I show the degree of attack in % of leaf area attacked, in comparison to untreated control plants.

Example II

Sugar beet plants in the 6-leaf stage were treated with the compounds claimed and mentioned in Example I, using amounts of 25, 12.5, 6.0 and 3.0 mg of active compound/liter of spray liquor until dripping wet. The comparison agent used was Benomyl employed in the same amounts. After the deposit of active compound had dried on, the plants were heavily infected with conidia of the pathogen of leaf spot disease (Cercospora beticola) and placed, dripping wet, in a climatically controlled chamber at a temperature of 25° C and a relative atmospheric humidity of 100%.

After a period of infection of 48 hours, the plants were brought into a greenhouse which was a relative atmospheric humidity of 85 –95% and a temperature of 25°–26° C. After an incubation time of 14 days, the plants were visually examined for attach by Cercospora. The degree of attack was expressed in % of attacked leaf area, relative to untreated infected control plants.

The result can be seen from Table II.

Example III

Sugar beet plants in the 6-leaf stage were heavily infected with conidia of the pathogen of leaf spot disease (Cercospora beticola). The plants were then placed dripping wet in an illuminated climatically controlled chamber which was at a temperature of 25° C and a relative atmospheric humidity of 100%. After an infection time of 5 days, the plants were taken out and after drying off they were treated with the claimed compounds mentioned in Example I, using amounts of 250, 125, 60 and 30 mg of active compound/liter of spray liquor, until dripping wet. The comparison agent used was Benomyl, employed in the same amounts.

After the deposit of active compound had dried on, the plants were brought into a greenhouse which was at a relative atmospheric humidity of 85 –95% and a temperature of 25°–26° C. After an incubation time of 14 days, the plants were examined visually for attack by Cercospora and the degree of attack was expressed in % of attacked leaf area relative to untreated infected control plants. The results are summarised in Table III.

Table I

| Compound according to Example | % of leaf area attacked by wheat mildew, when using mg of active compound/liter of spray liquor | | | |
|---|---|---|---|---|
| | 250 | 125 | 60 | 30 |
| 14 | 0 | 0 | 0 | 5 |
| 18 | 0 | 0 | 0 | 3 |
| 46 | 0 | 0 | 0 | 8 |
| Comparison agent, Benomyl | 0 | 0 | 5 | 15 |
| Untreated infected plants | 100 | 100 | 100 | 100 |

Table II

| Compound according to Example | % of leaf area attacked by Cercospora, when using mg of active compound/liter of spray liquor | | | |
|---|---|---|---|---|
| | 25 | 12.5 | 6.0 | 3.0 |
| 14 | 0 | 0 | 0 | 2 |
| 18 | 0 | 0 | 0 | 5 |
| 46 | 0 | 0 | 0 | 3 |
| Comparison agent, Benomyl | 0 | 0 | 5 | 12 |
| Untreated infected plants | 100 | 100 | 100 | 100 |

Table III

| Compound according to Example | % of leaf area attacked by Cercospora, when using mg of active compound/liter of spray liquor | | | |
|---|---|---|---|---|
| | 250 | 125 | 60 | 30 |
| 14 | 0 | 0 | 0 | 6 |
| 18 | 0 | 0 | 0 | 8 |
| 46 | 0 | 0 | 0 | 5 |
| Comparison agent, Benomyl | 0 | 0 | 5 | 12 |
| Untreated infected plants | 100 | 100 | 100 | 100 |

2. Pharmeceutical action

The active compounds, together with suitable pharmaceutical solvents or excipients, are administered orally or parenterally, one or other method of administration being preferred depending on the circumstances.

To determine the action of the compounds according to the invention, chemotherapeutic investigations on either sheep or dogs are carried out. The former are experimentally infected with larvae of Haemonchus contortus and Trichostrongylus colubriformis, and the latter with larvae of Ancylostoma canium. The test animals are kept in tiled boxes which are thoroughly cleaned daily to avoid superinfections. At the end of the pre-patency period (time between infection and sexual maturity of the parasites, with incipient elimination of reproduction products), the number of eggs per gram of faeces (EpG) are determined by a modified McMaster process (see Tierarztliche Umschau 6, 209 –210; 1951). Immediately thereafter, the animals - in general comprising four to eight animals per group, but at least two - are treated orally or parenterally, a suspension of 0.5 to 20.0 mg/kg of body weight in 10 ml of a tylose suspension (1% strength aqueous suspension) being administered. On the 7th, 14th and 28th day after the treatment, the number of eggs per gram of faeces is again determined in accordance with the abovementioned process and its change in percentage terms relative to the initial value before treatment is determined. In cases of convincing success, dissecton of the test animals and examination of the digestive tract for any nematodes present is optionally carried out.

The two tables which follow show the anthelmintic action of selected substances amongst the compounds claimed, as determined by the experimental method described above. The anthelmintic action of two known compounds of similar structure is listed by way of comparison.

The examples shown in the tables demonstrate the superiority of the products which have been described and claimed, relative to the comparison preparations, as manifesting itself in the lower minimum curative dose. The superiority of the process products claimed can optionally be demonstrated additionally through their action against trongylides of the stomach and intestine in ruminants or against Ancylostoma of carnivores.

The use concentration depends on the chosen form of administration. The total weight of the dosage units and their content of active compound from amongst substances claimed depend, within wide limits, on the species of animal treated, the desired dosage dose and the degree and nature of the parasitic attack. For larger animals, for example pigs, sheep and cattle, suspensions (1 –80% strength, particularly 3 –15% strength), powders which can be suspended in water (1 –80% strength, particularly 40 –70% strength), boli, pastes or granules of similarly broad concentration ranges can be used. For parenteral treatment, sterile liquid preparations (concentration 0.5 –50%, particularly 3 –25%) are used. In the case of solid and liquid preparations, additives, in amounts varying from case to case, are necessary for purposes of uniform distribution, stabilisation and preservation.

Table IV

Action of substituted monotriazinobenzimidazoles against strongylides of the stomach and intestine in sheep

| Compound according to Example | Dose, mg/kg, administered orally | Effect |
|---|---|---|
| 66 | <5 | 100% |
| 52 | <5 | 100% |
| 31 | <5 | 100% |
| 48 | 5 | >70% |
| 18 | <5 | 100% |
| 54 | <5 | 100% |
| 61 | <5 | 100% |
| 58 | <5 | 100% |
| 53 | <5 | 100% |
| 45 | 5 | >70% |
| 64 | 5 | >90% |
| 1 | <5 | 100% |
| 59 | <5 | 100% |
| 69 | <5 | 100% |
| Thiabendazol [+] | 50 | >99% |
| Parbendazol [++] | 15 | 100% |

[+] Thiabendazol: 2-(4-Thiazolyl)-benzimidazole Eaton, L.G. et al., (1969), Texas Rep. Biol. Med. 27, 693 – 708

[++] Parbendazol: 5-(6-)-Butyl-2-benzimidazolecarbamate Actor, P. et al. (1967); Nature 215, 321

Table V
Action of monosubstituted monotriazinobenzimidazoles against hookworms in dogs

| Compound according to Example | Dose, mg/kg, | Effect |
|---|---|---|
| 50 | 15 | >70% |
| 66 | 15 | >70% |
| 47 | 15 | >70% |
| 52 | <10 | 100% |
| 62 | 10 | >90% |
| 44 | 10 | >90% |
| 54 | 10 | >70% |
| 56 | 15 | >70% |
| 61 | 10 | >90% |
| 67 | <10 | 100% |
| 65 | 10 | >70% |
| 45 | 10 | >90% |
| 1 | <10 | 100% |
| Thiabendazol | 500 | 82% |
| Parabendazol | 100–200 | 77–93% |

Thiabendazol: 2-(4-Thiazolyl)-benzimidazole Novilla, M. N. and R. F. Flauta (1967); Philipp, J. Vet. Med. 6, 135 – 144

Parbendazol: 5-(6-)-Butyl-2-benzimidazolecarbamate Theodorakis, V. J. and M. Ladermann (1968); Vet. Med./Small Animal Clin. 63, 985

What we claim is:

1. A triazinobenzimidazole of the formula

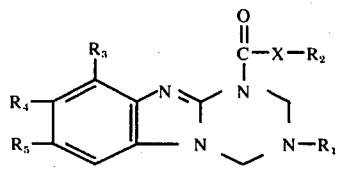

wherein $R_1$ is straight-chain or branched alkyl having 1 to 18 carbon atoms; straight-chain or branched alkenyl having 3 to 18 carbon atoms; cycloalkyl having 3 to 12 carbon atoms; cycloalkyl having 3 to 12 carbon atoms and substituted by at least one alkyl having 1 to 4 carbon atoms or by hydroxy; tricyclo-[5,2,1,0$^{2,6}$]-decyl; phenylalkyl or diphenylalkyl each having 1 to 6 carbon atoms in the alkyl; phenyl-substituted phenylalkyl or phenyl-substituted diphenylalkyl each having 1 to 6 carbon atoms in the alkyl and in which the substituents in the phenyl are halogen, alkyl having 1 to 4 carbon atoms, alkoxy having 1 to 4 carbon atoms, or alkylthio having 1 to 4 carbon atoms; phenyl; phenyl substituted by alkyl having 1 to 4 carbon atoms, halogen, halogenoalkyl having 1 to 4 carbon atoms, hydroxyl, alkoxy having 1 to 4 carbon atoms, phenoxy, or alkylthio having 1 to 4 carbon atoms; naphthyl; naphthyl substituted by alkyl having 1 to 4 carbon atoms, halogen, halogenoalkyl having 1 to 4 carbon atoms, hydroxyl, alkoxy having 1 to 4 carbon atoms, phenoxy, or alkylthio having 1 to 4 carbon atoms; furfuryl; or $R_1$ is hydroxyalkyl, alkoxyalkyl, polyalkoxyalkyl, alkyl mercaptoalkyl, dialkyl phosphinyl alkyl, morpholino alkyl, pyrrolidino alkyl, piperidino alkyl, or carbalkoxy alkyl each having 2 to 12 carbon atoms; or $R_1$ is dialkylaminoalkyl of the formula

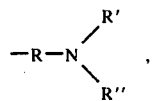

wherein R is straight-chain or branched alkylene having 2 to 6 carbon atoms and R' and R'' are the same or different alkyl having 1 to 4 carbon atoms; or is 1',1'-dialkyl-substituted propin-2'-yl of the formula

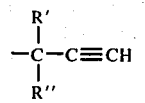

wherein R' and R'', taken alone, are alkyl having 1 to 4 carbon atoms, phenyl, or substituted phenyl, or wherein R' and R'', taken together, are 5- to 8-membered cycloalkyl substituted by alkinyl having 2 to 3 carbon atoms, or are bicycloheptenyl methyl, exo-bicycloheptylmethyl, endo-bicycloheptylmethyl, bicycloheptyl or tricyclo-decenyl;

$R_2$ is methyl;
$R_3$ is hydrogen;
$R_4$ is phenylthio;
$R_5$ is hydrogen; and
X is oxygen.

2. The compound of claim 1 in which $R_1$ is cyclohexyl.
3. The compound of claim 1 in which $R_1$ is isobutyl.
4. The compound of claim 1 in which $R_1$ is t-butyl.
5. The compound of claim 1 in which $R_1$ is benzyl.
6. The compound of claim 1 in which $R_1$ is dodecyl.
7. The compound of claim 1 in which $R_1$ is iso nonyl.
8. The compound of claim 1 in which $R_1$ is —CH(C$_6$H$_5$)CH$_2$C$_6$H$_5$.
9. The compound of claim 1 in which $R_1$ is tricyclo—(5,2,1,0) decyl.
10. The compound of claim 1 in which $R_1$ is —(CH$_2$)$_3$—SCH$_3$.
11. The compound of claim 1 in which $R_1$ is octadecyl.
12. The compound of claim 1 in which $R_1$ is octyl.
13. The compound of claim 1 in which $R_1$ is methyl.
14. The compound of claim 1 in which $R_1$ is phenyl. exo-bicycloheptylmethyl, endo-bicycloheptylmethyl, bicycloheptyl, or tricyclo-decenyl;

$R_2$ is methyl;
$R_3$ is hydrogen;
$R_4$ is phenylthio;
$R_5$ is hydrogen; and
X is oxygen.

15. A triazinobenzimidazole of the formula

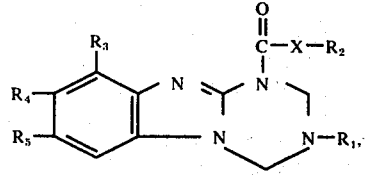

wherein $R_1$ is straight-chain or branched alkyl having 1 to 18 carbon atoms; straight-chain or branched alkenyl having 3 to 18 carbon atoms; cycloalkyl having 3 to 12 carbon atoms; cycloalkyl having 3 to 12 carbon atoms and substituted by at least one alkyl having 1 to 4 carbon atoms or by hydroxy; tricyclo [5,2,1,0$^{2,6}$]-decyl; phenylalkyl or diphenylalkyl each having 1 to 6 carbon atoms in the alkyl; phenyl-substituted phenylalkyl or phenyl-substituted diphenyalkyl each having 1 to 6 carbon atoms in the alkyl and in which the substituents in the phenyl are halogen, alkyl having 1 to 4 carbon atoms, alkoxy having 1 to 4 carbon atoms, or alkylthio having 1 to 4 carbon atoms, phenyl; phenyl substituted by alkyl having 1 to 4 carbon atoms, halogen, halogenoalkyl having 1 to 4 carbon atoms, hydroxyl, alkoxy having 1 to 4 carbon atoms, phenoxy, or alkylthio having 1 to 4 carbon atoms; naphthyl; naphthyl substituted by alkyl having 1 to 4 carbon atoms, halogen, halogenoalkyl having 1 to 4 carbon atoms, hydroxyl, alkoxy having 1 to 4 carbon atoms, phenoxy, or alkylthio having 1 to 4 carbon atoms, furfuryl; or $R_1$ is hydroxyalkyl, alkoxyalkyl, polyalkoxyalkyl, alkyl mercaptoalkyl, dialkyl phosphinyl alkyl, morpholino alkyl, pyrrolidino alkyl, piperidino akyl, carbalkoxy alkyl each having 2 to 12 carbon atoms; or $R_1$ is dialkylaminoalkyl of the formula

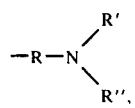

wherein R is straight-chain or branched alkylene having 2 to 6 carbon atoms and R' and R'' are the same or different alkyl having 1 to 4 carbon atoms; or is 1′,1′-dialkyl-substituted propin-2′-yl of the formula

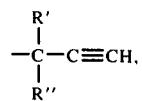

wherein R' and R'', taken alone, alkyl having 1 to 4 carbon atoms, phenyl, or substituted phenyl, or wherein R' and R'', taken together, are 5- to 8-membered cycloalkyl substituted by alkinyl having 2 to 3 carbon atoms, or are bicycloheptenyl methyl, exo-bicycloheptylmethyl, endo-bicycloheptylmethyl, bicycloheptyl, or tricyclo-decenyl;
$R_2$ is straight-chain or branched alkyl having 1 to 6 carbon atoms;
$R_3$ is chlorine or bromine;
$R_4$ is hydrogen, halogen, phenylthio, phenylsulfinyl, phenoxy, ethoxy, methyl, nitrile, quinolinoxy, N′-methylpiperazino, or benzoyl;
$R_5$ is hydrogen or halogen; and
X is oxygen or sulfur.

16. A triazinobenzimidazole of the formula

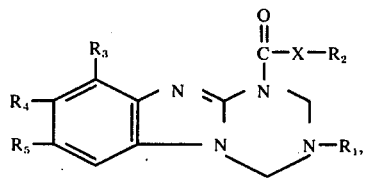

wherein $R_1$ is straight-chain or branched alkyl having 1 to 18 carbon atoms; straight-chain or branched alkenyl having 3 to 18 carbon atoms; cycloalkyl having 3 to 12 carbon atoms; cycloalkyl having 3 to 12 carbon atoms and substituted by at least one alkyl having 1 to 4 carbon atoms or by hydroxy; tricyclo-[5,2,1,0$^{2,6}$]-decyl; phenylalkyl or diphenylalkyl each having 1 to 6 carbon atoms in the alkyl; phenyl-substituted phenylalkyl or phenyl-substituted diphenylalkyl each having 1 to 6 carbon atoms in the alkyl and in which the substituents in the phenyl are halogen, alkyl having 1 to 4carbon atoms, alkoxy having 1 to 4 carbon atoms, or alkylthio having 1 to 4 carbon atoms; phenyl; phenyl substituted by alkyl having 1 to 4 carbon atoms, halogen, halogenoalkyl having 1 to 4 carbon atoms, hydroxyl, alkoxy having 1 to 4 carbon atoms, phenoxy, or alkylthio having 1 to 4 carbon atoms; naphthyl; naphthyl substituted by alkyl having 1 to 4 carbon atoms, halogen, halogenoalkyl having 1 to 4 carbon atoms, hydroxyl, alkoxy having 1 to 4 carbon atoms, phenoxy, or alkylthio having 1 to 4 carbon atoms; furfuryl; or $R_1$ is hydroxyalkyl, alkoxyalkyl, polyalkoxyalkyl, alkyl mercaptoalkyl, dialkyl phosphinyl alkyl, morpholino alkyl, pyrrolidino alkyl, piperidino alkyl, or carbalkoxy alkyl each having 2 to 12 carbon atoms; or $R_1$ is dialkylaminoalkyl of the formula

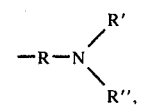

wherein R is straight-chain or branched alkylene having 2 to 6 carbon atoms and R' and R'' are the same or different alkyl having 1 to 4 carbon atoms; or is 1′,1′-dialkyl-substituted propin 2′-yl of the formula

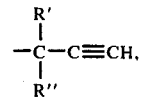

wherein R' and R'', taken alone are alkyl having 1 to 4 carbon atoms, phenyl, or substituted phenyl, or wherein R' and R'', taken together, are 5- to 8-membered cycloalkyl substituted by alkinyl having 2 to 3 carbon atoms, or are bicycloheptenyl methyl, exo-bicycloheptylmethyl, endo-bicycloheptylmethyl, bicycloheptyl, or tricyclo-decenyl;
$R_2$ is straight-chain or branched alkyl having 1 to 6 carbon atoms;
$R_3$ is hydrogen or halogen;
$R_4$ is fluorine, chlorine, or bromine;
$R_5$ is hydrogen or halogen; and
X is oxygen or sulfur.

17. A triazinobenzimidazole of the formula

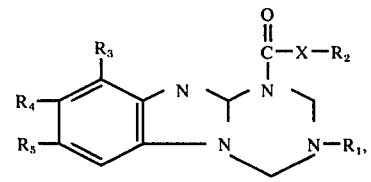

wherein $R_1$ is straight-chain or branched alkyl having 1 to 18 carbon atoms; straight-chain or branched alkenyl having 3 to 18 lcarbon atoms; cycloalkyl having 3 to 12 carbon atoms; cycloalkyl having 3 to 12 carbon atoms and substituted by at least one alkyl having 1 to 4 carbon atoms or by hydroxy; tricyclo[5,2,1,0$^{2,6}$]-decyl, phenylalkyl or diphenylalkyl each having 1 to 6 carbon atoms in the alkyl; phenyl-substituted phenylalkyl or phenyl-substituted diphenylalkyl each having 1 to 6 carbon atoms in the alkyl and in which the substituents in the phenyl are halogen, alkyl having 1 to 4 carbon atoms, alkoxy having 1 to 4 carbon atoms, or alkylthio having 1 to 4 carbon atoms; phenyl; phenyl substituted by alkyl having 1 to 4 carbon atoms, halogen, halogenoalkyl having 1 to 4 carbon atoms, hydroxyl, alkoxy having 1 to 4 carbon atoms, phenoxy, or alkylthio having 1 to 4 carbon atoms; naphthyl; naphthyl substituted by alkyl having 1 to 4 carbon atoms, halogen, halogenoalkyl having 1 to 4 carbon atoms, hydroxyl, alkoxy having 1 to 4 carbon atoms, phenoxy, or alkylthio having 1 to 4 carbon atoms; furfuryl; or $R_1$ is hydroxyalkyl, alkoxyalkyl, polyalkoxyalkyl, alkyl mercaptoalkyl, dialkyl phosphinyl alkyl, morpholino alkyl, pyrrolidino alkyl, piperidino alkyl, or carbalkoxy alkyl each having 2 to 12 carbon atoms; or $R_1$ is dialkylaminoalkyl of the formula

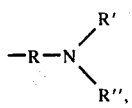

wherein R is straight-chain or branched alkylene having 2 to 6 carbon atoms and R' and R'' are the same or different alkyl having 1 to 4 carbon atoms; or is 1',1'-dialkyl-substituted propin-2'-yl of the formula

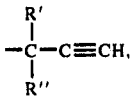

wherein R' and R'', taken alone, are alkyl having 1 to 4 carbon atoms, phenyl, or substituted phenyl, or wherein R' and R'', taken together, are 5- to 8-membered cycloalkyl substituted by alkinyl having 2 to 3 carbon atoms, or are bicycloheptenyl methyl, exo-bicycloheptylmethyl, endo-bicycloheptylmethyl, bicycloheptyl, or tricyclo-decenyl;

$R_2$ is straight-chain or branched alkyl having 1 to 6 carbon atoms;

$R_3$ is hydrogen or halogen;

$R_4$ is hydrogen, halogen, phenylthio, phenylsulfinyl, phenoxy, ethoxy, methyl, nitrile, quinolinoxy, N'-methyl-piperazino, or benzoyl; l $R_5$ is chlorine or bromine; and X is oxygen or sulfur.

* * * * *